(12) United States Patent
Ball et al.

(10) Patent No.: US 8,283,177 B2
(45) Date of Patent: Oct. 9, 2012

(54) FLUIDIC SYSTEM WITH WASHING CAPABILITIES FOR A FLOW CYTOMETER

(75) Inventors: Jack T. Ball, Ann Arbor, MI (US); Aaron Kehrer, Ypsilanti, MI (US); Nathaniel C. Bair, Ann Arbor, MI (US); Collin A. Rich, Ypsilanti, MI (US)

(73) Assignee: Accuri Cytometers, Inc., Ann Arbor, MI (US)

( * ) Notice: Subject to any disclaimer, the term of this patent is extended or adjusted under 35 U.S.C. 154(b) by 295 days.

(21) Appl. No.: 12/476,860

(22) Filed: Jun. 2, 2009

(65) Prior Publication Data

US 2009/0293910 A1 Dec. 3, 2009

Related U.S. Application Data

(63) Continuation-in-part of application No. 11/370,714, filed on Mar. 8, 2006, now Pat. No. 8,017,402.

(60) Provisional application No. 61/082,035, filed on Jul. 18, 2008, provisional application No. 61/088,660, filed on Aug. 13, 2008.

(51) Int. Cl.
*G01N 21/15* (2006.01)
*G01N 21/09* (2006.01)
*G01N 21/05* (2006.01)
*G01N 35/08* (2006.01)

(52) U.S. Cl. ............ 436/63; 436/164; 436/177; 422/73; 422/82.05; 422/400; 356/39; 356/246; 356/335; 435/286.5; 435/286.1

(58) Field of Classification Search ........................ None
See application file for complete search history.

(56) References Cited

U.S. PATENT DOCUMENTS

| | | |
|---|---|---|
| 3,347,273 A | 10/1967 | Russell |
| 3,601,128 A | 8/1971 | Hakim |
| 3,672,402 A | 6/1972 | Bloemer |
| 4,112,735 A | 9/1978 | Mcknight |
| 4,138,879 A | 2/1979 | Liebermann |
| 4,371,786 A | 2/1983 | Kramer |
| 4,448,538 A | 5/1984 | Mantel |
| 4,559,454 A | 12/1985 | Kramer |
| 4,570,639 A | 2/1986 | Miodownik |
| 4,691,829 A | 9/1987 | Auer |
| 4,755,021 A | 7/1988 | Dyott |
| 4,790,653 A | 12/1988 | North, Jr. |
| 4,818,103 A | 4/1989 | Thomas et al. |
| 4,824,641 A | 4/1989 | Williams |

(Continued)

FOREIGN PATENT DOCUMENTS

EP 466490 A 1/1992

(Continued)

*Primary Examiner* — P. Kathryn Wright
(74) *Attorney, Agent, or Firm* — Jeffrey Schox

(57) ABSTRACT

A method for cleaning a fluidic system of a flow cytometer having a sheath pump to pump sheath fluid towards an interrogation zone and a waste pump to pump the sheath fluid and a sample fluid as waste fluid from the interrogation zone, wherein the sheath pump and/or the waste pump draw sample fluid into the flow cytometer through a drawtube towards the interrogation zone. The method includes controlling the sheath pump and the waste pump to cooperatively flush a fluid out through the drawtube, thereby cleaning the fluidic system of the flow cytometer.

14 Claims, 7 Drawing Sheets

U.S. PATENT DOCUMENTS

| | | | |
|---|---|---|---|
| 4,826,660 A | 5/1989 | Smith et al. |
| 4,844,610 A | 7/1989 | North, Jr. |
| 4,933,813 A | 6/1990 | Berger |
| 5,028,127 A | 7/1991 | Spitzberg |
| 5,040,890 A | 8/1991 | North, Jr. |
| 5,043,706 A | 8/1991 | Oliver |
| 5,083,862 A | 1/1992 | Rusnak |
| 5,138,868 A | 8/1992 | Long |
| 5,139,609 A | 8/1992 | Fields et al. |
| 5,150,037 A | 9/1992 | Kouzuki |
| 5,150,313 A | 9/1992 | Van Den et al. |
| 5,155,543 A | 10/1992 | Hirako |
| 5,204,884 A | 4/1993 | Leary et al. |
| 5,224,058 A | 6/1993 | Mickaels et al. |
| 5,230,026 A | 7/1993 | Ohta et al. |
| 5,270,548 A | 12/1993 | Steinkamp |
| 5,301,685 A | 4/1994 | Guirguis |
| 5,308,990 A | 5/1994 | Takahashi et al. |
| 5,367,474 A | 11/1994 | Auer et al. |
| 5,374,395 A | 12/1994 | Robinson et al. |
| 5,395,588 A | 3/1995 | North, Jr. et al. |
| 5,403,552 A | 4/1995 | Pardikes |
| 5,466,946 A | 11/1995 | Kleinschmitt et al. |
| 5,469,375 A | 11/1995 | Kosaka |
| 5,539,386 A | 7/1996 | Elliott |
| 5,552,885 A | 9/1996 | Steen |
| 5,559,339 A | 9/1996 | Domanik et al. |
| 5,616,124 A | 4/1997 | Hague et al. |
| 5,684,480 A | 11/1997 | Jansson |
| 5,739,902 A | 4/1998 | Gjelsnes et al. |
| 5,797,430 A | 8/1998 | Becke et al. |
| 5,798,222 A | 8/1998 | Goix |
| 5,804,507 A | 9/1998 | Perlov et al. |
| 5,883,378 A | 3/1999 | Irish et al. |
| 5,920,388 A | 7/1999 | Sandberg et al. |
| 5,960,129 A | 9/1999 | Kleinschmitt |
| 5,981,180 A | 11/1999 | Chandler et al. |
| 6,016,376 A | 1/2000 | Ghaemi et al. |
| 6,039,078 A | 3/2000 | Tamari |
| 6,067,157 A | 5/2000 | Altendorf |
| 6,070,477 A | 6/2000 | Mark |
| 6,091,502 A | 7/2000 | Weigl et al. |
| 6,097,485 A | 8/2000 | Lievan |
| 6,108,463 A | 8/2000 | Herron et al. |
| 6,110,427 A | 8/2000 | Uffenheimer |
| 6,115,065 A | 9/2000 | Yadid-Pecht et al. |
| 6,139,800 A | 10/2000 | Chandler |
| 6,154,276 A | 11/2000 | Mariella, Jr. |
| 6,156,208 A | 12/2000 | Desjardins et al. |
| 6,181,319 B1 | 1/2001 | Fujita et al. |
| 6,183,697 B1 | 2/2001 | Tanaka et al. |
| 6,288,783 B1 | 9/2001 | Auad |
| 6,377,721 B1 | 4/2002 | Walt et al. |
| 6,382,228 B1 | 5/2002 | Cabuz et al. |
| 6,403,378 B1 | 6/2002 | Phi-Wilson et al. |
| 6,427,521 B2 | 8/2002 | Jakkula et al. |
| 6,431,950 B1 | 8/2002 | Mayes |
| 6,456,769 B1 | 9/2002 | Furusawa et al. |
| 6,469,787 B1 | 10/2002 | Meyer et al. |
| 6,473,171 B1 | 10/2002 | Buttry et al. |
| 6,519,355 B2 | 2/2003 | Nelson |
| 6,522,775 B2 | 2/2003 | Nelson |
| 6,568,271 B2 | 5/2003 | Shah et al. |
| 6,587,203 B2 | 7/2003 | Colon |
| 6,602,469 B1 | 8/2003 | Maus et al. |
| 6,636,623 B2 | 10/2003 | Nelson et al. |
| 6,675,835 B2 | 1/2004 | Gerner et al. |
| 6,694,799 B2 | 2/2004 | Small |
| 6,700,130 B2 | 3/2004 | Fritz |
| 6,710,871 B1 | 3/2004 | Goix |
| 6,718,415 B1 | 4/2004 | Chu |
| 6,778,910 B1 | 8/2004 | Vidal et al. |
| 6,809,804 B1 | 10/2004 | Yount et al. |
| 6,816,257 B2 | 11/2004 | Goix |
| 6,825,926 B2 | 11/2004 | Turner et al. |
| 6,852,284 B1 | 2/2005 | Holl et al. |
| 6,859,570 B2 | 2/2005 | Walt et al. |
| 6,869,569 B2 | 3/2005 | Kramer |
| 6,872,180 B2 | 3/2005 | Reinhardt et al. |
| 6,890,487 B1 | 5/2005 | Sklar et al. |
| 6,897,954 B2 | 5/2005 | Bishop et al. |
| 6,901,964 B2 | 6/2005 | Kippe et al. |
| 6,908,226 B2 | 6/2005 | Siddiqui et al. |
| 6,912,904 B2 | 7/2005 | Storm, Jr. et al. |
| 6,936,828 B2 | 8/2005 | Saccomanno |
| 6,941,005 B2 | 9/2005 | Lary et al. |
| 6,944,322 B2 | 9/2005 | Johnson et al. |
| 7,009,189 B2 | 3/2006 | Saccomanno |
| 7,012,689 B2 | 3/2006 | Sharpe |
| 7,019,834 B2 | 3/2006 | Sebok et al. |
| 7,024,316 B1 | 4/2006 | Ellison et al. |
| 7,061,595 B2 | 6/2006 | Cabuz et al. |
| 7,075,647 B2 | 7/2006 | Christodoulou |
| 7,105,355 B2 | 9/2006 | Kurabayashi et al. |
| 7,106,442 B2 | 9/2006 | Silcott et al. |
| 7,113,266 B1 | 9/2006 | Wells |
| 7,130,046 B2 | 10/2006 | Fritz et al. |
| 7,232,687 B2 | 6/2007 | Lary et al. |
| 7,262,838 B2 | 8/2007 | Fritz |
| 7,274,316 B2 | 9/2007 | Moore |
| 7,328,722 B2 | 2/2008 | Rich et al. |
| 7,362,432 B2 | 4/2008 | Roth |
| 7,403,125 B2 | 7/2008 | Rich |
| 7,471,393 B2 | 12/2008 | Trainer |
| 7,520,300 B2 | 4/2009 | Rich et al. |
| 7,628,956 B2 | 12/2009 | Jindo |
| 7,738,099 B2 | 6/2010 | Morrell et al. |
| 7,739,060 B2 | 6/2010 | Goebel et al. |
| 7,776,268 B2 | 8/2010 | Rich |
| 7,780,916 B2 | 8/2010 | Bair et al. |
| 7,843,561 B2 | 11/2010 | Rich |
| 7,857,005 B2 | 12/2010 | Rich et al. |
| 7,981,661 B2 | 7/2011 | Rich |
| 7,996,188 B2 | 8/2011 | Olson et al. |
| 8,017,402 B2 | 9/2011 | Rich |
| 8,031,340 B2 | 10/2011 | Rich et al. |
| 2001/0014477 A1 | 8/2001 | Pelc et al. |
| 2001/0039053 A1* | 11/2001 | Liseo et al. ..................... 436/43 |
| 2002/0028434 A1 | 3/2002 | Goix et al. |
| 2002/0049782 A1 | 4/2002 | Herzenberg et al. |
| 2002/0059959 A1 | 5/2002 | Qatu et al. |
| 2002/0080341 A1 | 6/2002 | Kosaka |
| 2002/0123154 A1 | 9/2002 | Burshteyn et al. |
| 2002/0192113 A1 | 12/2002 | Uffenheimer et al. |
| 2003/0035168 A1 | 2/2003 | Qian et al. |
| 2003/0048539 A1 | 3/2003 | Oostman et al. |
| 2003/0054558 A1 | 3/2003 | Kurabayashi et al. |
| 2003/0062314 A1 | 4/2003 | Davidson et al. |
| 2003/0072549 A1 | 4/2003 | Facer et al. |
| 2003/0078703 A1 | 4/2003 | Potts et al. |
| 2003/0129090 A1 | 7/2003 | Farrell |
| 2003/0134330 A1 | 7/2003 | Ravkin et al. |
| 2003/0148379 A1 | 8/2003 | Roitman et al. |
| 2003/0175157 A1 | 9/2003 | Micklash, II et al. |
| 2003/0202175 A1 | 10/2003 | Van Den et al. |
| 2003/0211009 A1 | 11/2003 | Buchanan |
| 2003/0223061 A1 | 12/2003 | Sebok et al. |
| 2003/0235919 A1 | 12/2003 | Chandler |
| 2004/0031521 A1 | 2/2004 | Vrane et al. |
| 2004/0048362 A1 | 3/2004 | Trulson et al. |
| 2004/0112808 A1 | 6/2004 | Takagi et al. |
| 2004/0119974 A1 | 6/2004 | Bishop et al. |
| 2004/0123645 A1 | 7/2004 | Storm et al. |
| 2004/0131322 A1 | 7/2004 | Ye et al. |
| 2004/0143423 A1 | 7/2004 | Parks et al. |
| 2004/0175837 A1 | 9/2004 | Bonne et al. |
| 2004/0201845 A1 | 10/2004 | Quist et al. |
| 2004/0246476 A1 | 12/2004 | Bevis et al. |
| 2005/0044110 A1 | 2/2005 | Herzenberg et al. |
| 2005/0047292 A1 | 3/2005 | Park et al. |
| 2005/0057749 A1 | 3/2005 | Dietz et al. |
| 2005/0069454 A1 | 3/2005 | Bell |
| 2005/0073686 A1 | 4/2005 | Roth et al. |
| 2005/0078299 A1 | 4/2005 | Fritz et al. |
| 2005/0105091 A1 | 5/2005 | Lieberman et al. |
| 2005/0162648 A1 | 7/2005 | Auer et al. |
| 2005/0163663 A1 | 7/2005 | Martino et al. |

| | | |
|---|---|---|
| 2005/0195605 A1 | 9/2005 | Saccomanno et al. |
| 2005/0195684 A1 | 9/2005 | Mayer |
| 2005/0252574 A1 | 11/2005 | Khan et al. |
| 2006/0002634 A1 | 1/2006 | Riley et al. |
| 2006/0015291 A1 | 1/2006 | Parks et al. |
| 2006/0023219 A1 | 2/2006 | Meyer et al. |
| 2006/0161057 A1 | 7/2006 | Weber et al. |
| 2006/0177937 A1 | 8/2006 | Kurabayashi et al. |
| 2006/0219873 A1 | 10/2006 | Martin et al. |
| 2006/0281143 A1 | 12/2006 | Liu et al. |
| 2006/0286549 A1 | 12/2006 | Sohn et al. |
| 2007/0003434 A1 | 1/2007 | Padmanabhan et al. |
| 2007/0041013 A1 | 2/2007 | Fritz et al. |
| 2007/0096039 A1 | 5/2007 | Kapoor et al. |
| 2007/0124089 A1 | 5/2007 | Jochum et al. |
| 2007/0127863 A1 | 6/2007 | Bair et al. |
| 2007/0144277 A1 | 6/2007 | Padmanabhan et al. |
| 2007/0212262 A1 | 9/2007 | Rich |
| 2007/0224684 A1 | 9/2007 | Olson et al. |
| 2007/0243106 A1 | 10/2007 | Rich |
| 2008/0055595 A1 | 3/2008 | Olson et al. |
| 2008/0064113 A1 | 3/2008 | Goix et al. |
| 2008/0092961 A1 | 4/2008 | Bair et al. |
| 2008/0152542 A1 | 6/2008 | Ball |
| 2008/0215297 A1 | 9/2008 | Goebel et al. |
| 2008/0228444 A1 | 9/2008 | Olson et al. |
| 2009/0104075 A1 | 4/2009 | Rich |
| 2009/0174881 A1 | 7/2009 | Rich |
| 2009/0201501 A1 | 8/2009 | Bair et al. |
| 2009/0202130 A1 | 8/2009 | George et al. |
| 2009/0216478 A1 | 8/2009 | Estevez-Labori |
| 2009/0260701 A1 | 10/2009 | Rich et al. |
| 2010/0012853 A1 | 1/2010 | Parks et al. |
| 2010/0032584 A1 | 2/2010 | Dayong et al. |
| 2010/0118298 A1 | 5/2010 | Bair et al. |
| 2010/0119298 A1 | 5/2010 | Huang |
| 2010/0302536 A1 | 12/2010 | Ball et al. |
| 2010/0319469 A1 | 12/2010 | Rich |
| 2010/0319786 A1 | 12/2010 | Bair et al. |
| 2011/0008816 A1 | 1/2011 | Ball et al. |
| 2011/0058163 A1 | 3/2011 | Rich |
| 2011/0061471 A1 | 3/2011 | Rich et al. |
| 2011/0306031 A1 | 12/2011 | Rich |

FOREIGN PATENT DOCUMENTS

| | | | |
|---|---|---|---|
| EP | 1391611 A | | 2/2004 |
| EP | 1396736 A | | 3/2004 |
| EP | 1521076 A | | 4/2005 |
| JP | 356169978 | | 12/1981 |
| JP | 04086546 H | | 3/1992 |
| JP | 6-194299 | * | 7/1994 |
| JP | 06221988 H | | 12/1994 |
| JP | 7260084 A | | 10/1995 |
| JP | 08-201267 | * | 8/1996 |
| JP | 08201267 H | | 8/1996 |
| JP | 09-2888053 | * | 11/1997 |
| JP | 09288053 H | | 11/1997 |
| JP | 10227737 A | | 8/1998 |
| JP | 2001050887 A | | 2/2001 |
| JP | 2001170062 A | | 6/2001 |
| JP | 2003262201 A | | 9/2003 |
| JP | 200477484 | | 3/2004 |
| WO | 9956052 | | 11/1999 |
| WO | 0194914 | | 12/2001 |
| WO | 2005017499 A | | 2/2005 |
| WO | 2005068971 A | | 7/2005 |
| WO | 2005073694 A | | 8/2005 |
| WO | 2005091893 A | | 10/2005 |
| WO | 2006055722 A | | 5/2006 |
| WO | 2007/136749 | | 5/2007 |
| WO | 2007067577 A | | 6/2007 |
| WO | 2007100723 A | | 9/2007 |
| WO | 2007103969 A | | 9/2007 |
| WO | 2008058217 A | | 5/2008 |
| WO | 2010101623 A | | 9/2010 |

* cited by examiner

FLUIDIC SYSTEM WITH WASHING CAPABILITIES FOR A FLOW CYTOMETER

CROSS-REFERENCE TO RELATED APPLICATIONS

This application is a continuation in part of prior application Ser. No. 11/370,714 filed on 8 Mar. 2006, which is incorporated in its entirety by this reference.

This application also claims the benefit of both U.S. Provisional Application No. 61/082,035 filed on 18 Jul. 2008 and U.S. Provisional Application No. 61/088,660 filed on 13 Aug. 2008, which are both incorporated in their entirety by this reference.

TECHNICAL FIELD

This invention relates generally to the flow cytometer field, and more specifically to an improved fluidic system in the flow cytometer field.

BACKGROUND

The fluidic system of a conventional flow cytometer incorporates an air and/or vacuum pump to pressurize and pump sheath fluid from a high-pressure container to the interrogation zone of a flow cell. These fluidic systems are typically arduous to assemble (which increases the costs of the flow cytometer), heavy to haul (which limits the repair options), and challenging to calibrate (which induces errors in the data).

A conventional flow cytometer uses a drawtube to draw in a sample fluid. The drawtube draws in a sample fluid through direct contact with the sample fluid. Since old sample remnants and contaminants left in the drawtube can alter the results for future samples, it is important to insure a clean drawtube when switching between different samples. Conventional flow cytometers typically require manual washing (which requires the presence of the user before starting different sample).

Thus, there is a need in the flow cytometer field to create an improved fluidic system, one in which the fluidic system can also wash the drawtube. This invention provides such an improved fluidic system with washing capabilities for a flow cytometer.

DESCRIPTION OF THE PREFERRED EMBODIMENT

The following description of the preferred embodiment of the invention is not intended to limit the invention to this preferred embodiment, but rather to enable any person skilled in the art of flow cytometers to make and use this invention.

1. Sheath Pump, Waste Pump, and Controller

Figure 1:
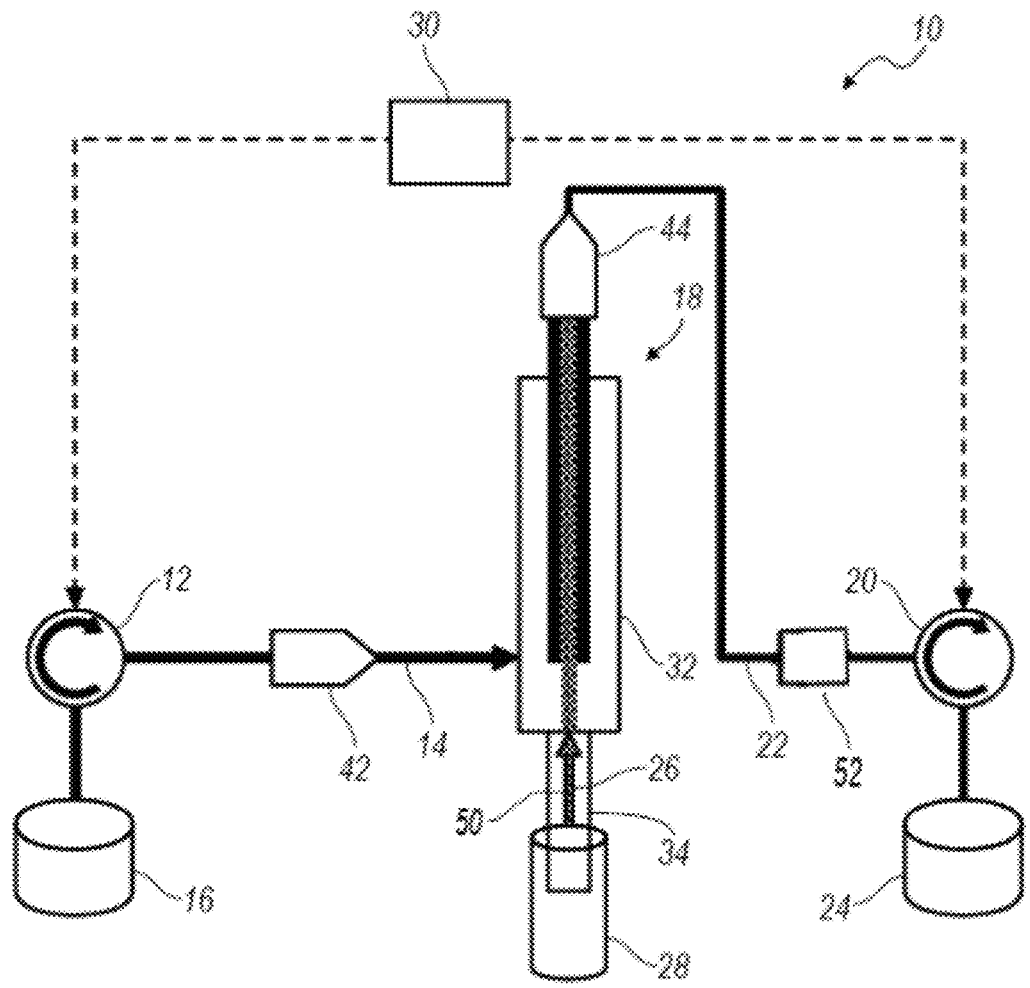
FIG. 1 is a schematic representation of the fluidic system of the preferred embodiment of the invention.

As shown in FIG. 1, the fluidic system 10 of the preferred embodiment includes a sheath pump 12 to pump sheath fluid 14 from a sheath container 16 into an interrogation zone 18 and a waste pump 20 to pump the sheath fluid 14 and a sample fluid 26 as waste fluid 22 from the interrogation zone 18 into a waste container 24. The sheath pump 12 and/or the waste pump 20 draw sample fluid 26 from a sample container 28 into the interrogation zone 18. The fluidic system 10 also includes a controller 30 to adjust the flow rate of the sample fluid 26 from the sample container 28 into the interrogation zone 18. The interrogation zone 18 functions to provide a location for the fluidic system 10 and an optical system of the flow cytometer to cooperatively facilitate the analysis of the sample fluid 26. The interrogation zone 18 is preferably enclosed within a removable flow cell 32, but may alternatively be defined by any suitable system or device. The fluidic system 10 is preferably incorporated into a flow cytometer, but may be alternatively incorporated into any suitable system that pumps a first fluid from a first container into an interrogation zone, draws a second fluid from a second container into the interrogation zone, and pumps the combined fluids from the interrogation zone into a third container.

The sheath pump 12 of the preferred embodiment functions to pump sheath fluid 14 from a sheath container 16 into an interrogation zone 18. The sheath fluid 14 functions to hydrodynamically focus the sample fluid 26. The process of hydrodynamic focusing results in laminar flow of the sample fluid 26 within the flow cell 32 and enables the optical system to illuminate, and thus analyze, the particles within the sample fluid 26 with uniformity and repeatability. Preferably, the sheath fluid 14 is buffered saline or de-ionized water, but the sheath fluid 14 may alternatively be any suitable fluid to hydrodynamically focus the sample fluid 26. The sheath container 16 functions to contain the sheath fluid 14. The sheath container 16 is preferably a vented tank with a volume of approximately 1 L, but the sheath tank may alternatively be any suitable container to contain the sheath fluid 14. Preferably, the sheath pump 12 is a positive displacement pump. More preferably, the sheath pump 12 is a peristaltic pump with a flexible tube and one or more cams that pump the sheath fluid 14 through the flexible tube. The sheath pump 12 preferably has a known flow rate to pump speed ratio, such that control of the speed of the sheath pump 12 corresponds to a control of the flow rate of the sheath fluid 14. With this pump type, the fluidic system 10 is relatively easy to assemble, light to haul, quick to control, and easy to clean. Alternatively, the sheath pump 12 may be any suitable pump that pumps sheath fluid 14 from a sheath container 16 into an interrogation zone 18.

The waste pump 20 of the preferred embodiment functions to pump the waste fluid 22 from the interrogation zone 18 into a waste container 24. Preferably, the waste fluid 22 includes the sheath fluid 14 and the sample fluid 26. Alternatively, the waste fluid 22 may include any fluid that exits the interrogation zone 18. The waste container 24 is preferably a vented tank with a volume of approximately 1 L, but the waste tank may alternatively be any suitable container to contain the waste fluid 22. Like the sheath pump 12, the waste pump 20 is preferably a positive displacement pump and more preferably a peristaltic pump with a flexible tube and one or more cams that pump the waste fluid 22 through the flexible tube. The waste pump 20 preferably has a known flow rate to pump speed ratio, such that control of the speed of the waste pump 20 corresponds to a control of the flow rate of the waste fluid 22. With this pump type, the fluidic system 10 is relatively easy to assemble, light to haul, quick to control, and easy to clean. Alternatively, the waste pump 20 may be any suitable pump that pumps waste fluid 22 from an interrogation zone 18 into an interrogation zone.

The sheath pump 12 and the waste pump 20 of the preferred embodiment cooperate to draw the sample fluid 26 from the sample container 28 and through a drawtube 34. The sample fluid 26 contains particles to be analyzed by the flow cytometer. The sample fluid 26 is preferably blood, but the sample fluid 26 may alternatively be any suitable fluid to be analyzed by the flow cytometer. The sample container 28, which functions to contain the sample fluid 26, is preferably an open beaker with a volume of approximately 5 mL, but may alternatively be any suitable container to contain the sample fluid 26. The drawtube 34, functions to convey the sample fluid 26 from the sample container 28 into the interrogation zone 18, is a conventional drawtube, but may alternatively be any suitable device to convey the sample fluid 26.

The sheath pump 12 and the waste pump 20 preferably cooperate to draw the sample fluid 26 from the sample container 28 into the interrogation zone 18 through the use of a pressure differential (e.g., the sheath pump 12 "pushes" the sheath fluid 14 and the waste pump 20 "pulls" the sheath fluid 14 and the sample fluid 26). In order to allow a variable flow rate of the sample fluid 26, the fluidic system 10 preferably allows for a variable flow rate of the sheath fluid 14 and/or the waste fluid 22. In a first variation, the sheath pump 12 and the waste pump 20 are driven by a single motor, but with a variable drive ratio device (e.g., transmission), such that the sheath pump 12 and the waste pump 20 may be operated at different pump speeds and, therefore, allow for a variable flow rate of the sheath fluid 14 and/or the waste fluid 22. In a second variation, the sheath pump 12 and the waste pump 20 are driven by a single motor, but the fluidic system 10 includes at least one by-pass valve located near the sheath pump 12 and/or the waste pump 20. The by-pass valve diverts a variable amount of the fluid flow and, therefore, allows for a variable flow rate of the sheath fluid 14 and/or waste fluid 22. In a third variation, the sheath pump 12 and the waste pump 20 are driven by a single motor, but the fluidic system 10 includes at least one restrictive valve located near the sheath pump 12 and/or the waste pump 20. The restrictive valve alters the fluid flow and, therefore, allows for a variable flow rate of the sheath fluid 14 and/or waste fluid 22. In a fourth variation, the sheath pump 12 and the waste pump 20 are driven by separate motors with separate controls and, therefore, allows for a variable flow rate of the sheath fluid 14 and/or waste fluid 22. The fluidic system 10 may, however, include other suitable variations that draw the sample fluid 26 from the sample container 28 into the interrogation zone 18 through the use of a pressure differential.

The controller 30 of the preferred embodiment functions to adjust the flow rate of the sample fluid 26 from the sample container 28 into the interrogation zone 18. The controller 30 may additionally or alternatively adjust the flow rate of a fluid through the drawtube 34. Preferably, the controller 30 adjusts the flow rate of the sample fluid 26 by adjusting the variable flow rate of the sheath fluid 14 and/or the waste fluid 22. More preferably, the controller 30 adjusts the flow rate of the sample fluid 26 by allowing an adjustable flow rate of the sheath fluid 14 from the sheath container 16 to the interrogation zone 18, while maintaining a consistent flow rate of the waste fluid 22 from the interrogation zone 18 into the waste container 24. The advantage of this arrangement is a finer control of the flow rate of the sample fluid 26. Alternatively, the controller 30 may adjust the flow rate of waste fluid 22 while maintaining the flow rate of the sheath fluid 14, or may simultaneously adjust the flow rates of the sheath fluid 14 and the waste fluid 22. Furthermore, the controller 30 may employ one technique (such as allowing an adjustable flow rate of the sheath fluid 14, while maintaining a consistent flow rate of the waste fluid 22) in most situations, and may employ another technique (such as simultaneously adjusting the flow rates of the sheath fluid 14 and the waste fluid 22) in other situations to quickly response to a user input. The controller 30 is preferably a proportional-integral-derivative (PID) controller, but may alternatively be a proportional-integral (PI) controller, a proportional-derivative (PD) controller, a proportional (P) controller, or any other suitable controller.

The fluidic system 10 of the preferred embodiment also includes a valve 42 located between the first fluidic capacitor and the interrogation zone 18, and a valve 44 located between the interrogation zone 18 and the second fluidic capacitor. The valves 42 and 44 function to facilitate the control of the sheath fluid 14 and the waste fluid 22. The valves 42 and 44 are preferably check-valves, but may alternatively be any suitable valve to facilitate the control of the sheath fluid 14 and the waste fluid 22.

The fluidic system 10 of the preferred embodiment is preferably operated with the following steps: (1) pumping sheath fluid 14 from a sheath container 16 into an interrogation zone 18 and pumping the sheath fluid 14 and the sample fluid 26 as waste fluid 22 from the interrogation zone 18 into a waste container 24, thereby drawing sample fluid 26 from a sample container 28 into the interrogation zone 18; and (2) adjusting the flow rate of the sample fluid 26 from the sample container 28 into the interrogation zone 18. As explained above, step (2) preferably includes allowing a substantially adjustable flow rate of the sheath fluid 14 from the sheath container 16 to the interrogation zone 18, while maintaining a substantially consistent flow rate of the waste fluid 22 from the interrogation zone 18 into the waste container 24. The operation of the fluidic system 10 also preferably includes attenuating pulsations within the sheath fluid 14 and the waste fluid 22.

2. Washing Capabilities

Figure 2:
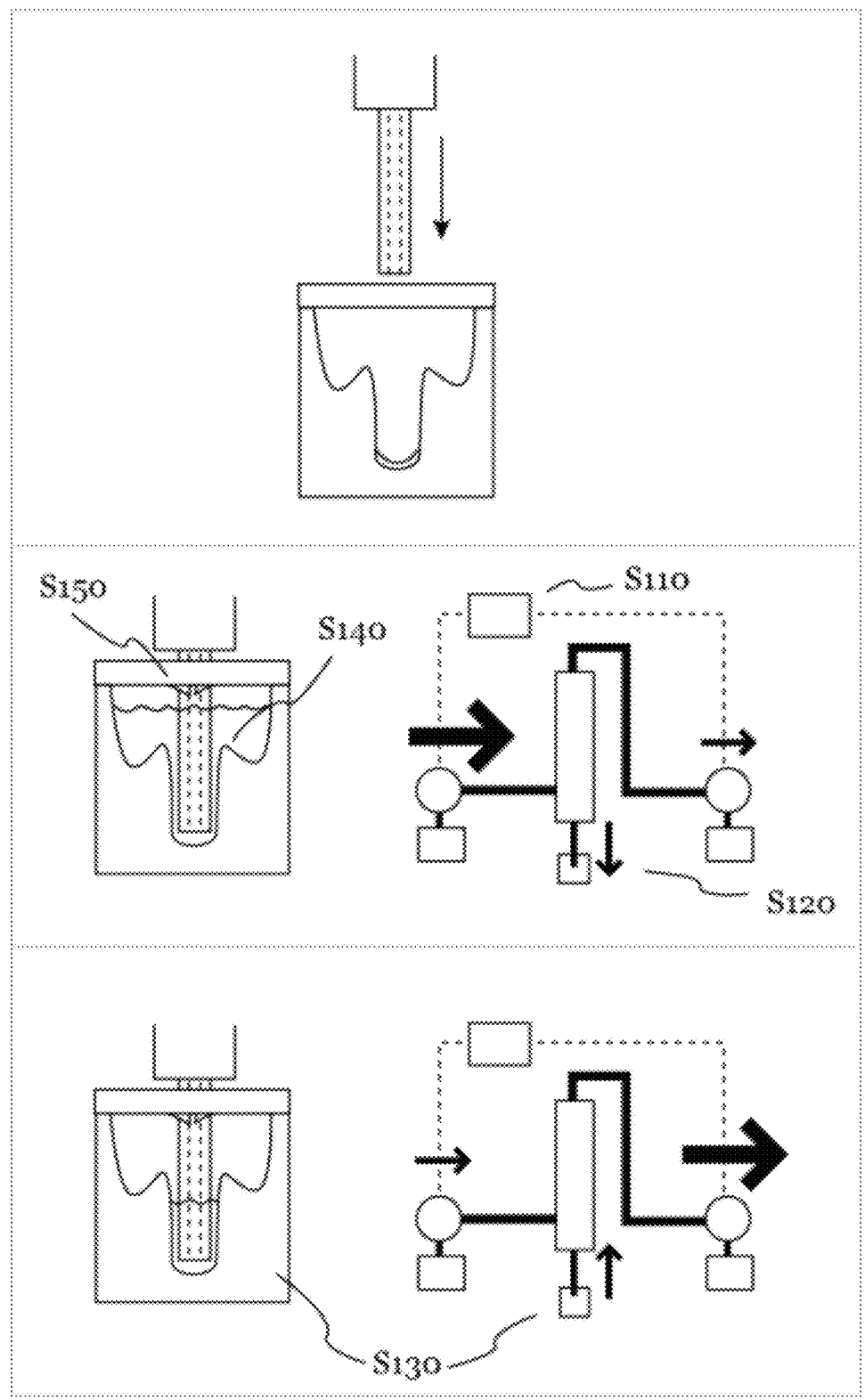
FIG. 2 is a depiction of an embodiment of the preferred washing method.
Figure 3:
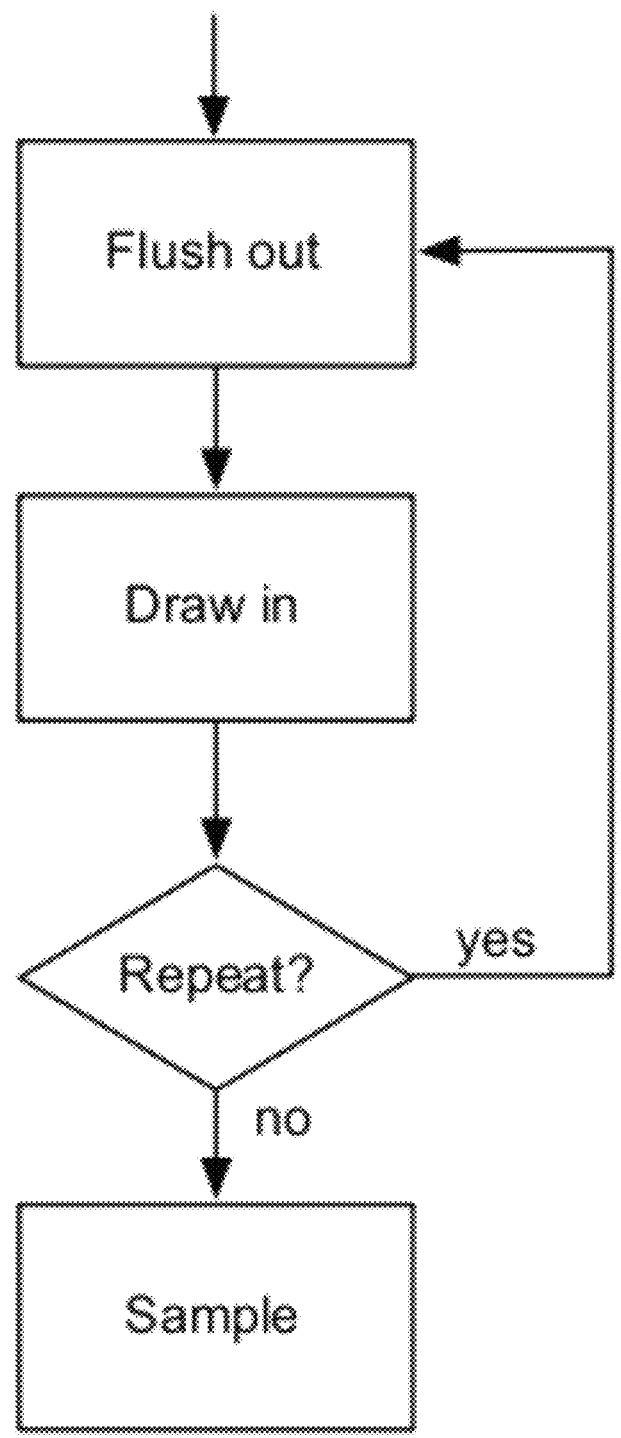
FIGS. 3 and 4 are flow diagrams of an embodiment of the preferred washing method.
Figure 4:
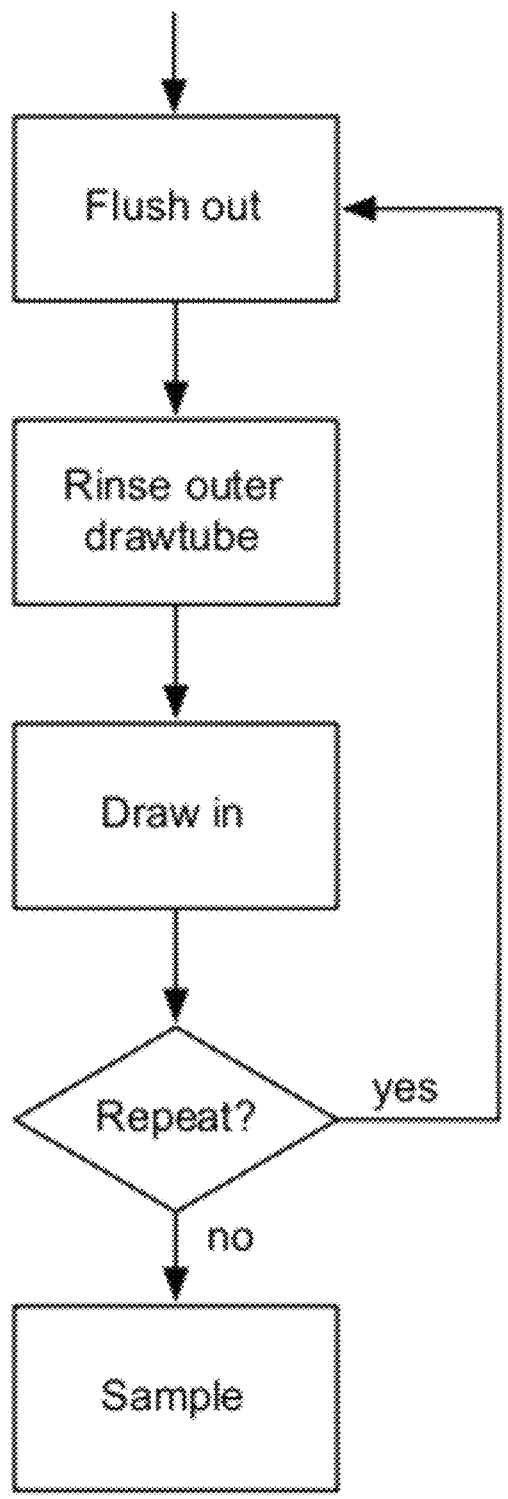

As shown in FIGS. 2-4, the invention also includes a method of washing the drawtube of the fluidic system 10. A first embodiment of the method includes the steps: controlling a sheath pump and waste pump of a fluidic system S110 and flushing a fluid out through the drawtube S120, thereby cleaning the fluidic system of the flow cytometer. The method functions to use a fluidic system to clean contaminates off a drawtube. The fluidic system is preferably substantially similar to the fluidic system used to draw in samples, and more preferably is substantially similar to the fluidic system described above. The sheath pump and waste pump preferably cooperate to direct the flow of fluid while flushing out fluid from the drawtube and while drawing in fluid through the drawtube.

Step S110, which includes controlling a sheath pump and waste pump of a fluidic system, functions to adjust the flow rate of a sheath fluid 14 and waste fluid 22 to alter the flow rate and direction of a fluid through the drawtube 34. The sheath pump 12 and waste pump 20 are preferably part of a fluidic system substantially similar to the fluidic system described above in design and/or operation. The sheath pump 12 and the waste pump 20 preferably cooperate to draw in or expel (flush out) a fluid through the drawtube 34 through the use of a pressure differential (e.g., to draw in, the sheath pump 12 "pushes" the sheath fluid 14 and the waste pump 20 "pulls" the sheath fluid 14 and the sample fluid 26). In order to allow a variable flow rate of the sample fluid 26, the fluidic system 10 preferably allows for a variable flow rate of the sheath fluid 14 and/or the waste fluid 22. The sheath pump 12 and the waste pump 20 are preferably positive displacement pumps and more preferably each peristaltic pump has a flexible tube and one or more cams that pump the sheath fluid 14 or waste fluid 22 through the flexible tube. The sheath pump 12 and the waste pump 20 preferably have a known flow rate to pump speed ratio, such that control of the speed of the sheath pump 12 or waste pump 20 corresponds to a control of the flow rate of the sheath fluid 14 or waste fluid 22. Alternatively, the waste pump 20 may be any suitable pump that pumps waste fluid 22 from a waste container 24 into an interrogation zone 18.

Step S120, which includes flushing out the drawtube, functions to remove unwanted sample remnants or contaminants from the inside capillary 50 of the drawtube 34. The step of flushing out the drawtube is preferably accomplished by pushing out sample and/or sheath fluid (instead of drawing in sample fluid). During the flushing out step, the sheath fluid 14 pressure is set greater than the waste fluid 22 pressure, which flushes the sheath fluid 14 out the drawtube 34. Another way of describing this is the flow rate of the sheath fluid 22 through the sheath pump 12 is greater than the flow rate of the waste fluid 22 through the waste pump 20. This is preferably achieved by pumping a sheath fluid 14 at a first flow rate, and pumping waste fluid 22 from the interrogation zone at a second flow rate, such that the first flow rate is less than the second flow rate. Alternatively, to achieve a second flow rate less than the first flow rate, the waste pump 20 may be stopped (set at a zero value), or—in some cases—may even be reversed (set at a negative value). The sheath pump 12 and waste pump 20 are preferably fluidically connected such that the pressure differences alters fluid flow in the fluidic system (and thus through the drawtube 34). Ideally, the sheath fluid 34 will flow through the drawtube 34 and remove unwanted sample remnants or contaminants from the inside capillary 50 of the drawtube 34. Preferably, as described above, the sheath pump 12 and waste pump 20 are peristaltic pumps, and the controller 30 creates a pressure differential by pumping sheath fluid with the sheath pump 12 and stopping (or even reversing) fluid flow with the waste pump 20. Alternatively, the controller 30 can continue to run the sheath pump 12 and waste pump 20 (in a "positive" direction from the interrogation zone to the waste tank), but at rates such that the sheath fluid 14 pressure is greater than the waste fluid 22 pressure. As another alternative, a stop valve 52 may be positioned between the interrogation zone 18 and the waste pump 20. The stop valve 52 ceases or decreases the pressure of the waste fluid 22 below that of the sheath fluid 14, thereby significantly limiting waste fluid 22 from flowing from the interrogation zone 18 to the waste pump 20. The stop valve 52 is preferably a pneumatic valve, but may alternatively be any suitable valve to facilitate the flushing out of the fluidic system. As an additional alternative the waste pump 20 may have a flow rate in the negative direction (towards the interrogation zone), and fluid is preferably flushed out as long as the flow rate of the sheath fluid 14 is greater than the flow rate of waste fluid 22.

An additional or alternative step of the preferred embodiment includes drawing in cleaning fluid 54 S130. This additional step allows for a more thorough washing of the drawtube 34 as the cleaning fluid 54 can be run through the entire fluidic system 10 after flushing out. The drawing in step is preferably achieved by operating the sheath and waste pumps in the same manner as when sampling as described above. In particular, drawing in a cleaning fluid S130 may include pumping a sheath fluid towards the interrogation zone of the flow cytometer at a sheath fluid flow rate and pumping waste fluid from the interrogation zone at a waste fluid flow rate, such that the sheath fluid flow rate is less than the waste fluid flow rate. Preferably, the cleaning fluid 54 drawn into the fluidic system 10 is the expelled sheath fluid 14. Alternatively, it could be a secondary cleaning fluid 54 such as deionized water, saline solution, bleach, or any other suitable fluid for cleaning the fluidic system. In the preferred embodiment, the method also includes aligning a wash station 56 under the drawtube 34 during the washing. The wash station 56 preferably defines a cavity 58 that functions to hold sheath fluid 14 expelled from the fluidic system 10 after flushing out. The wash station 56 is preferably made of plastic, rubber, or any other suitable material. The end of the drawtube 56 is preferably extended down into the cavity 58. The flushing out and drawing in steps are preferably repeated multiple times. In a variation of the method, the cavity 58 may contain a cleaning agent 60 inside the cavity 58 such that expelled sheath fluid 14 mixes with the cleaning agent 60. The cleaning agent 60 and sheath fluid 14 in combination add additional further cleaning capabilities when drawn in. The cleaning agent 60 is preferably any additive that may contribute to the cleaning of the fluidic system, such as bleach. The cleaning agent 60 may be a powder, a liquid, a gel, a solid, and/or any suitable form that may be mixed with the sheath fluid 14. The expelling of the sheath fluid 14 into the wash station 56 preferably contributes to the mixing of the sheath fluid 14 and the cleaning agent 60.

An additional or alternative step of the preferred embodiment includes drawing in a sample fluid. The controller 30 can preferably initiate pulling a sample fluid into the fluidic system 10. This step functions to draw in a fluid from the drawtube 34 and facilitate an investigation of the sample. Preferably a sample container 28 is aligned beneath the drawtube 34 and then is pulled into the fluidic system 10 through the drawtube 34. The controller 30 preferably sets the sheath pump 12 and waste pump 20 pressure such that the sheath fluid 14 pressure is less than that of the waste fluid 22 pressure, which will draw up a sample fluid 26 through the drawtube 34 to the flow cell 32. Another way of describing this is the flow rate of the sheath fluid 22 through the sheath pump 12 is less than the flow rate of the waste fluid 14 through the waste pump 20. This is preferably achieved by turning on the waste pump 20 while continuing to run the sheath pump 12. The step of flushing out can optionally be performed before every new sample fluid 26 is sampled.

An additional or alternative step of the preferred embodiment includes washing the outside of the drawtube 34 S140. Since the drawtube directly contacts the sample fluid, this step functions to prevent contamination of the subsequent sample fluid by the remnants of the previous sample fluid on the outside of the drawtube. In the preferred embodiment, a cleaning fluid 54 functions to wash the outside of the drawtube 34. The cleaning fluid 54 is preferably the expelled sheath fluid. The wash station 56 facilitates this step by providing the cavity 58 that can be filled to a height sufficient for expelled sheath fluid 14 to wash a significant portion of the outside of the drawtube 34. The drawtube 34 is preferably positioned (or inserted) in the cavity 58 so the expelled sheath fluid 14 can rise to the top of the cavity 58. The step of drawing in is preferably performed after this step, and all the expelled sheath fluid is drawn into the fluidic system. Unwanted sample remnants or contaminants from the outside of the drawtube are preferably washed away with the cleaning fluid 54.

An additional or alternative step of the preferred embodiment includes wiping the outside of the drawtube 34 S150. This step functions to remove contaminates on the outside of the drawtube 34. A drawtube scrubber 112 is preferably used to abrasively wipe the outside of the drawtube. As the drawtube 34 is being inserted into the cavity 58 of the wash station 56, the drawtube 34 preferably penetrates (i.e., passes through) the material of the drawtube scrubber 112 and thereby removes contaminants. The drawtube 34 may additionally or alternatively, wipe contaminates off during the removal of the drawtube 34 from the wash station 56, absorb contaminates, disinfect contaminates, or any suitable process that removes or neutralizes contaminates on the outside of the drawtube 34.

3. The Wash Station

Figure 5:
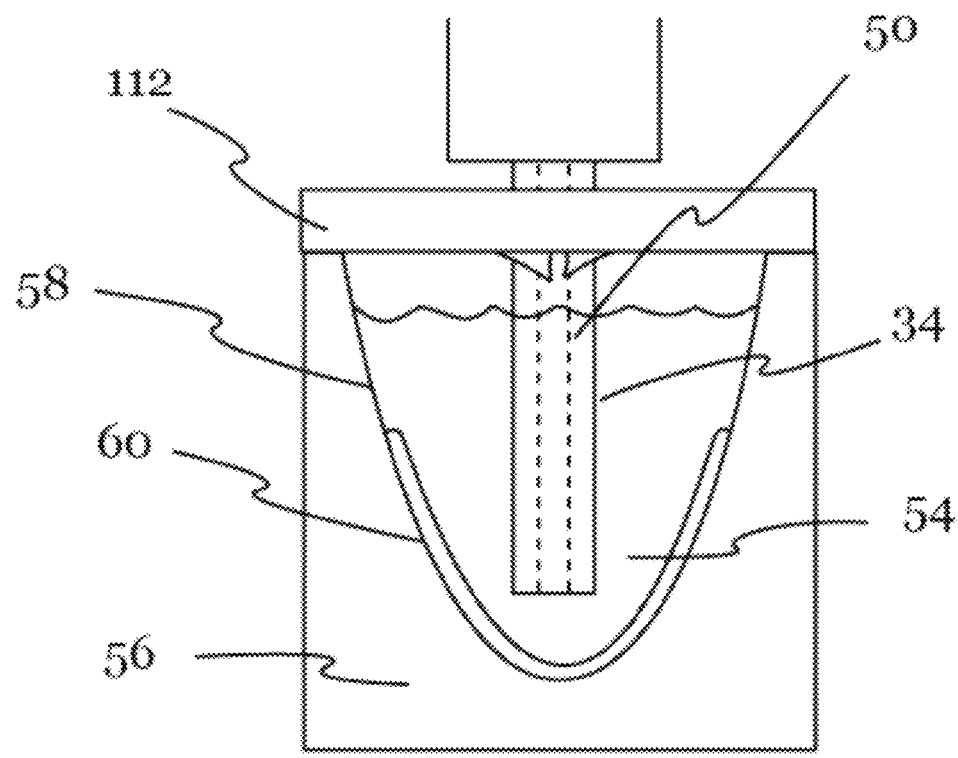
FIGS. 5-7 are schematic views of the washing station of a preferred embodiment of the invention.
Figure 6:
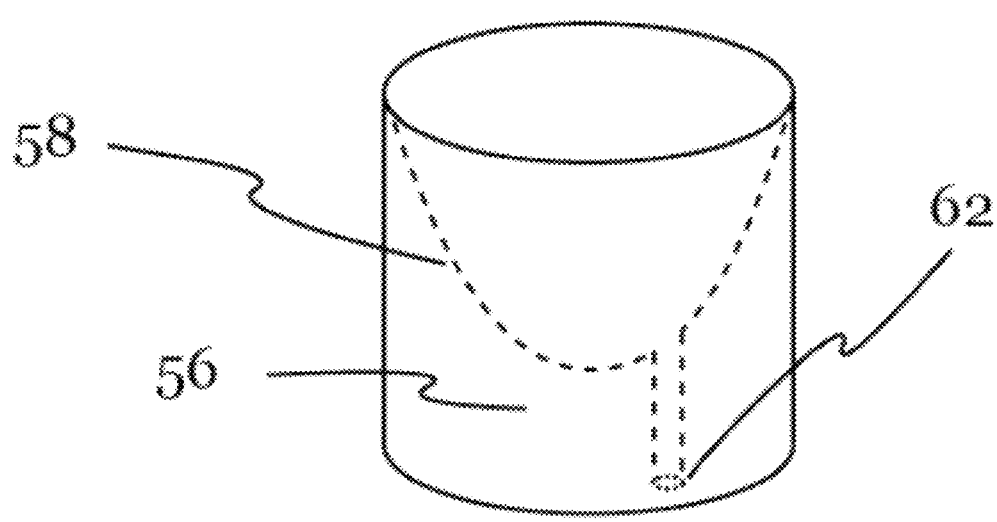
Figure 7:
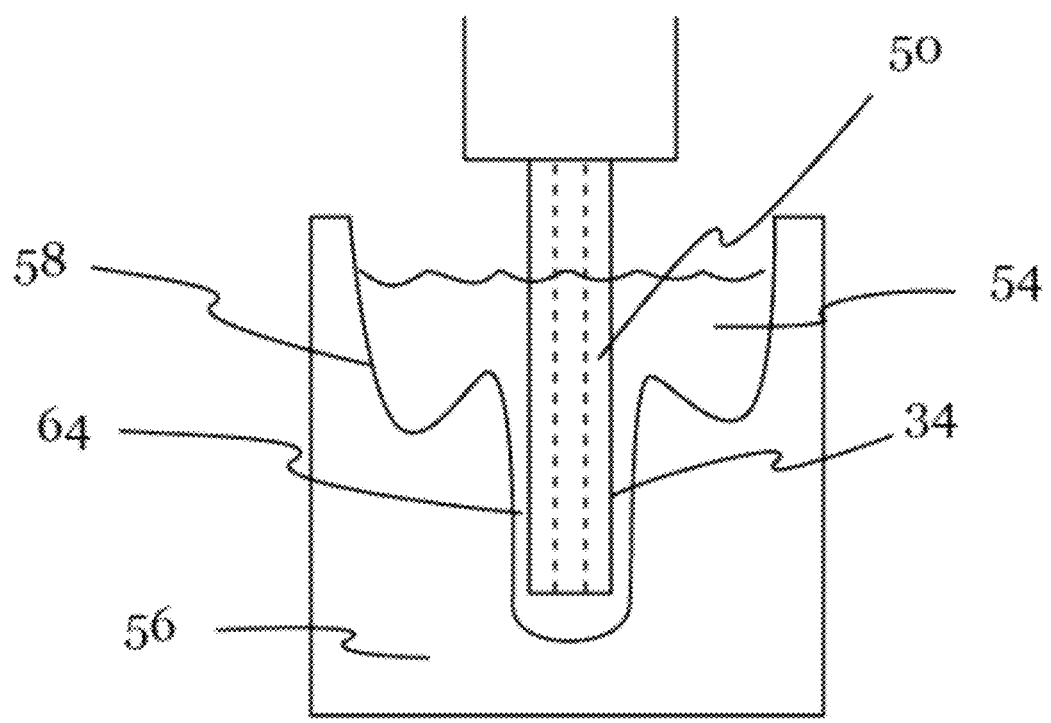

As shown in FIG. 5, the wash station 56 of the preferred embodiment functions to receive sheath fluid 14 expelled through the drawtube 34. The design of the wash station 56 preferably facilitates the washing of the drawtube 34 and the drawing in of cleaning fluid 54. The cavity 58 preferably has a width, depth, and shape sufficient to allow the drawtube 34 to be inserted to the bottom of the wash station 56. The cavity 58 can preferably be filled with a cleaning fluid 54 to a depth sufficient to rinse the outside of the drawtube 34. In one variation, the cavity 58 is convex in shape with a generally singular low point. Here, convex cavity 58 is preferably understood to describe any cavity that convexly extends into the wash station 56, such that the walls of the wash station 56 are concave. The cavity 53 is preferably conical shaped but may alternatively be a pyramid, have a cylindrical, parabolic or elliptical sides or any suitable form that functions to receive sheath fluid 14 expelled through the drawtube 34. The cavity may alternatively have any suitable shape that facilitates the cleaning of the drawtube 34. The drawtube is preferably extended to the bottom of the wash station to the low point. The convex shape functions to minimize the amount of cleaning fluid 54 in the wash station 56 after the cleaning fluid 54 is drawn into the drawtube 34. In another variation, as depicted in FIG. 6, the wash station 56 defines a hole 62 at the bottom of the cavity 58 to function as a drain for the cleaning fluid 54. Preferably, the hole 62 is sufficiently small that the rate of draining is less than the flow rate of expelled sheath fluid 14. This allows the wash station 56 to be filled with sheath fluid 14 but over time the sheath fluid 14 will drain out through the hole 62. This allows sheath fluid 14 to optionally be expelled and drawn back into the drawtube 34 or to only be expelled. As shown in FIG. 7, the cavity 58 may be designed so that the drawtube 34 has a small gap 64 between the cavity 58 and the drawtube 34. The small gap 46 is preferably a fluidic channel defined by the outside surface of the drawtube 34 and a wall off the convex cavity 58. The small gap 64 is designed so the volume defined by the small gap 64 is approximately equal to that of the inner capillary 50 of the drawtube 34. This small gap 64 functions to maintain the fluidic pressure along the outside of the drawtube 34 as well as the inner capillary 50. A second cavity (or region of the convex cavity 58) may additionally be used for collection of fluids pumped through the small gap. The wash station 56 is preferably located in close proximity to the drawtube 34 so that cleaning may be readily performed before, during, or after an experiment. The wash station 56 is preferably positioned within a sampling area of a flow cytometer, such that the wash station 56 and drawtube 56 may be automatically aligned for the cleaning process. The wash station 56 may alternatively be part of a well plate or attached to a well plate or any suitable sample test container.

As shown in FIG. 5, the wash station 56 may additionally include a drawtube scrubber 112. The drawtube scrubber 112 functions to wipe and/or abrasively clean the outside surface of the drawtube 34 prior to inserting the drawtube 34 into the wash station 56. The drawtube scrubber 112 is preferably a layer of material attached above the cavity of the wash station that the drawtube 34 must pass through. The drawtube scrubber 112 may alternatively be positioned to the side of the wash station such as an embodiment that separates the cleaning process of the probe into multiple steps. As the drawtube 34 is being inserted into the cavity of the wash station 56, the drawtube 34 preferably penetrates (i.e., passes through) the material of the drawtube scrubber 112 and thereby removes contaminants. The drawtube 34 may additionally or alternatively, wipe contaminates off during the removal of the drawtube 34 from the wash station 56, absorb contaminates, disinfect contaminates, or any suitable process that removes or neutralizes contaminates on the outside of the drawtube 34.

Figure 8:
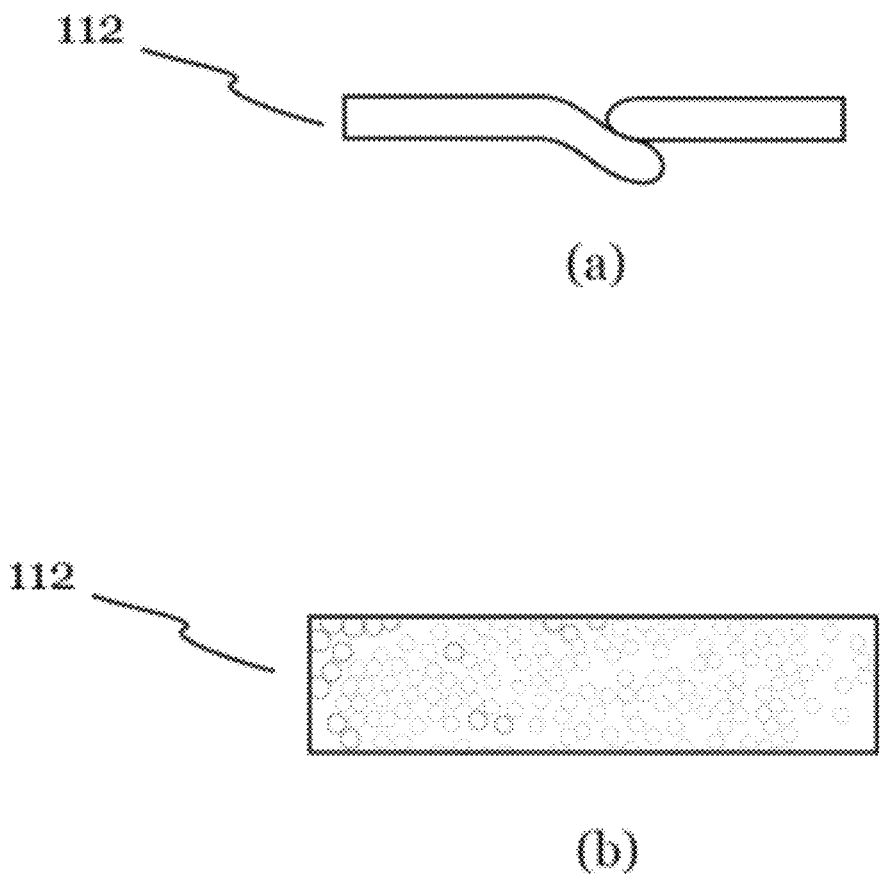
FIGS. 8(a) and 8(b) are detailed schematic views of two variations of a drawtube scrubber.

As shown in FIG. 8b, one variation of the drawtube scrubber 112 is a block of penetrable material. The drawtube 34 is preferably inserted in varying locations of the drawtube scrubber 112 to prevent wearing down of material of the drawtube scrubber 112. The drawtube scrubber 112 is preferably a block of material that allows insertion of a significant portion of the drawtube 34. The material of the drawtube scrubber 112 is preferably hydrophilic to absorb any liquid sample. Though, alternatively, the drawtube scrubber 112 may be made of silicon, a sponge, foam, or any suitable material that is penetrable and may aid in cleaning of the drawtube 34. In another variation, the drawtube scrubber 112 may be a container of small particulate material (like sand or grit) that acts to be abrasive and absorptive. The small particulate material is preferably displaced by the drawtube 34 with minimal pressure exerted by the drawtube 34. The small particulate material may be contained in a mesh like container above the wash station 56 or may alternatively fill the convex cavity 58 of the wash station 56.

As shown in FIG. 8a, a second preferred variation of the drawtube scrubber 112 may alternatively be a film positioned across the top of the wash station 56. During insertion and removal, the friction between the drawtube 34 and the film preferably removes contaminants from the drawtube 34. Alternatively and/or additionally, the well plate film 104 may be made of an absorbent material that absorbs any excess fluid either on or in the drawtube 34. The drawtube scrubber 112 may additionally be replaceable such that after the drawtube scrubber degrades or reaches an end of a lifecycle, a new drawtube scrubber 112 may be attached to the wash station 56. Preferably the drawtube scrubber 112 is mechanically attached to the top of the wash station 56, but the drawtube scrubber 112 may alternatively be elastically fit, rest in the cavity, be adhesively attached, or attached in any suitable manner. The film is preferably made of silicon or alternatively, polyethylene, latex, mylar foil, aluminum foil, or any other suitable material. Alternatively, the film may be made from multiple layers of similar or different materials. The drawtube 34 preferably pierces through the surface of the film. The drawtube scrubber 112 may additionally or alternatively include a flap valve 116 that functions to allow the drawtube to pass through the film without piercing the material. After the drawtube 106 is withdrawn, the flap valve 116 then folds up to seal the opening when the drawtube 34 is not present. The flap valve 116 is preferably formed by having a slit in the film. A portion of the film material (the "lip") extends past and under the slit. The pressure of the drawtube 34 pressing on the lip causes the lip to fold downward, allowing the drawtube 34 to pass through the slit. But when no pressure is exerted by the drawtube 34 or outside means, the natural state of the lip is preferably pressed against the slit, thereby sealing the slit. Additionally, the lip preferably facilitates wiping the outside of the drawtube 34 clean of contaminants. Alternatively, the flap valve 116 may be a circular hole that is pressed closed by internal stresses in the well plate film material or may be any suitable valve with a preexisting opening that can be accessed by exerting pressure with the SIP.

As a person skilled in the art of flow cytometers will recognize from the previous detailed description and from the figures and claims, modifications and changes can be made to the preferred embodiment of the invention without departing from the scope of this invention defined in the following claims.

We claim:

1. A method for cleaning a fluidic system of a flow cytometer having a sheath pump to pump sheath fluid towards an interrogation zone and a waste pump to pump the sheath fluid and a sample fluid as waste fluid from the interrogation zone, wherein the sheath pump and/or the waste pump draw sample fluid into the flow cytometer through a drawtube towards the interrogation zone, comprising:
    controlling the sheath pump and the waste pump to cooperatively flush a fluid out through the drawtube, thereby cleaning the fluidic system of the flow cytometer, including: pumping sheath fluid towards the interrogation zone of the flow cytometer at a first flow rate; and pumping waste fluid from the interrogation zone at a second flow rate; wherein the first flow rate is greater than the second flow rate; and
    drawing in a cleaning fluid, including: pumping sheath fluid towards the interrogation zone of the flow cytometer at a third flow rate; and pumping waste fluid from the interrogation zone at a fourth pump flow rate; wherein the third flow rate is less than the fourth flow rate.

2. The method of claim 1, further including depositing flushed out fluid into a wash station.

3. The method of claim 2, further including inserting the drawtube into the wash station.

4. The method of claim 3, further including wiping the outside of the drawtube with a drawtube scrubber.

5. The method of claim 4, wherein the drawtube scrubber is a film that abrasively rubs against the drawtube as the drawtube is inserted into the wash station.

6. The method of claim 3, further including rinsing the outside of the drawtube in fluid collected in a convex cavity of the wash station.

7. The method of claim 6, further including pumping fluid through a channel created by the outside of the drawtube and the walls of the cavity of the wash station.

8. The method of claim 1, wherein the first flow rate and the third flow rate are different flow rates.

9. The method of claim 1, wherein the second flow rate is approximately zero.

10. The method of claim 1, wherein drawing in a cleaning fluid includes:
    drawing in a cleaning fluid that comprises at least one of sheath fluid flushed out of the drawtube and a cleaning agent in a wash station.

11. A method for cleaning a fluidic system of a flow cytometer having a sheath pump to pump sheath fluid towards an interrogation zone and a waste pump to pump the sheath fluid and a sample fluid as waste fluid from the interrogation zone, wherein the sheath pump and/or the waste pump draw sample fluid into the flow cytometer through a drawtube towards the interrogation zone, comprising:
    controlling the sheath pump and the waste pump to cooperatively flush a fluid out of the fluidic system through the drawtube, thereby cleaning the fluidic system of the flow cytometer, including: pumping sheath fluid towards the interrogation zone of the flow cytometer at a first flow rate and pumping waste fluid from the interrogation zone at a second flow rate, wherein the first flow rate is greater than the second flow rate; and
    drawing in a cleaning fluid that is a mixture of sheath fluid flushed out of the drawtube and a cleaning agent in a wash station, wherein drawing in a cleaning fluid includes: pumping sheath fluid towards the interrogation zone of the flow cytometer at a third flow rate; and pumping waste fluid from the interrogation zone at a fourth pump flow rate; wherein the third flow rate is less than the fourth flow rate.

12. The method of claim 11, further comprising inserting the drawtube into the wash station and depositing flushed out fluid into a wash station.

13. The method of claim 11, wherein the first flow rate and the third flow rate are different flow rates.

14. The method of claim 11, wherein the second flow rate is approximately zero.

* * * * *